(12) United States Patent
Hidaka et al.

(10) Patent No.: US 7,750,182 B2
(45) Date of Patent: *Jul. 6, 2010

(54) PROCESS FOR PRODUCTION OF IODINE COMPOUNDS AND PROCESS FOR PRODUCTION OF HIGH-PURITY 5-IODO-2-METHYLBENZOIC ACID

(75) Inventors: Toshio Hidaka, Niigata (JP); Takafumi Yoshimura, Niigata (JP); Yoshifumi Sato, Niigata (JP); Norio Fushimi, Okayama (JP); Masaharu Doya, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/545,005

(22) PCT Filed: Feb. 10, 2004

(86) PCT No.: PCT/JP2004/001367

§ 371 (c)(1),
(2), (4) Date: Mar. 2, 2006

(87) PCT Pub. No.: WO2004/069772

PCT Pub. Date: Aug. 19, 2004

(65) Prior Publication Data

US 2006/0161028 A1 Jul. 20, 2006

(30) Foreign Application Priority Data

Feb. 10, 2003 (JP) .............................. 2003-032187
Feb. 10, 2003 (JP) .............................. 2003-032671

(51) Int. Cl.
*C07C 17/00* (2006.01)
*C07C 63/04* (2006.01)

(52) U.S. Cl. ....................................... 562/493; 570/203

(58) Field of Classification Search ................. 560/103; 562/493, 494; 570/182, 203, 206, 211, 243, 570/246, 247, 261

See application file for complete search history.

(56) References Cited

U.S. PATENT DOCUMENTS

| 4,746,758 | A | * | 5/1988 | Rule et al. | 570/206 |
| 4,778,939 | A | * | 10/1988 | Tustin et al. | 570/203 |
| 4,778,940 | A | * | 10/1988 | Rule et al. | 570/203 |
| 4,788,354 | A | * | 11/1988 | Paparatto et al. | 570/203 |
| 4,788,355 | A | * | 11/1988 | Rule | 570/203 |
| 4,792,641 | A | * | 12/1988 | Rule et al. | 570/202 |
| 4,792,642 | A | * | 12/1988 | Rule et al. | 570/203 |
| 4,806,697 | A | * | 2/1989 | Rule et al. | 570/202 |

FOREIGN PATENT DOCUMENTS

| EP | 0 181 790 | 5/1986 |
| EP | 0 183 579 | 6/1986 |
| EP | 0 273 736 | 7/1988 |
| EP | 0 333 436 A1 | 9/1989 |
| EP | 1 642 881 | 4/2006 |
| JP | 59-219241 | 12/1984 |
| JP | 59-219241 A | 12/1984 |
| JP | 1-502819 A | 9/1989 |
| JP | 3-503412 A | 8/1991 |
| JP | 08-157394 | 6/1996 |
| JP | 8-157394 A | 6/1996 |
| JP | 2003-012597 | 1/2003 |
| JP | 2003-12597 A | 1/2003 |
| WO | WO 88/02358 | 4/1988 |
| WO | WO 88/07509 | 10/1988 |

OTHER PUBLICATIONS

Kirk-Othmer Encyclopedia of Chemical Technology Copyright © 2001 by John Wiley & Sons pp. 95-147.*
Carruthers et al., Journal of the Chemical Society, Perkin Transactions 1: Organic and Bio-Organic Chemistry (1972-1999) (1974), (20), 2405-9.*
Alexander et al., Synlett (2003), (12), 1895-1897.*

(Continued)

*Primary Examiner*—Karl J Puttlitz
(74) *Attorney, Agent, or Firm*—Antonelli, Terry, Stout & Kraus, LLP.

(57) ABSTRACT

Provided is a production method for an iodine compound in which iodine is reacted with a substrate in the presence of a porous material having a pore diameter of 500 nm or less or in the presence of the above porous material and an oxidizing agent and a production process for high purity 5-iodo-2-methylbenzoic acid comprising an iodination reaction step carried out by the above-mentioned, a crystal precipitation and separation step in which a product is precipitated by adding water or cooling and then separated and a purification step in which crystal separated is recrystallized using an organic solvent. According to the production method for an iodine compound described above, iodine can be introduced into various substrates at a high selectivity. Since expensive metals and specific reagents do not have to be used, it can readily be carried out in an industrially scale, and the product having a high purity can be obtained. Further, the process comprising the iodination reaction, separation and purification steps described above makes it possible to readily obtain at a high yield, 5-iodo-2-methylbenzoic acid having a high purity which is useful in uses for functional chemical products such as medicines. The process of the present invention comprising iodination reaction, separation and purification steps is characterized by that it is simple in terms of a procedure and that the purification load is smaller, and it is very advantageous in industrially carrying out.

10 Claims, No Drawings

OTHER PUBLICATIONS

Tilve et al., Tetrahedron Letters (2002), 43(51), 9457-9459.*
Pagni et al., Journal of Organic Chemistry (1988), 53(19), 4477-82.*
Boothe et al., Tetrahedron Letters (1986), 27(20), 2207-10.*
Chinese Office Action Aug. 25, 2006, for Application No. 200480003902.5.
Supplementary European Search Report, for Application No. EP 04 70 9714, dated Mar. 6, 2007.

* cited by examiner

PROCESS FOR PRODUCTION OF IODINE COMPOUNDS AND PROCESS FOR PRODUCTION OF HIGH-PURITY 5-IODO-2-METHYLBENZOIC ACID

This application is a National Stage application filed under 35 USC 371 of International (PCT) Application No. PCT/JP2004/001367, filed Feb. 10, 2004.

BACKGROUND OF THE INVENTION

The present invention relates to a direct and selective production method for an iodine compound using iodine and a production process for high purity 5-iodo-2-methylbenzoic acid. Iodine compounds are important compounds, which are widely used as medicines such as contrast media and therapeutic agents for thyroid disease, sanitary materials for the purpose of anti-fungus and anti-mildew, electronic materials, optically functional materials, etching agents, catalysts and materials for chemical reactions in the fields of life science, electro-, info-communication, environment and energy. And high purity 5-iodo-2-methylbenzoic acid is a useful compound as a raw material for various performance chemicals in addition to medicines and agricultural chemicals.

RELATED ART

Compounds containing fluorine or iodine atoms have characteristics which are not observed in the other halogen-containing compounds. For example, a fluorine atom has a small size and a large electro-negativity, and therefore the stability of bonds and the revelation of physiological activity which originate therein allow them to be used in various fields including medical and electronic materials. On the other hand, an iodine atom has a large size and is an amphoteric element, and it assumes many oxidation states. It has a low oxidation potential as compared with those of fluorine, chlorine and bromine, and therefore revelation of various reactivities and functions can be expected. In addition thereto, ionic iodine has a low toxicity and therefore is widely used in many fields related to medicines, electronics and communication, environment and energy.

Publicly well known iodination techniques include, for example, direct iodination by iodine or iodine monochloride, vapor phase oxyiodination and a method in which compounds having halogen atoms are subjected to halogen-iodine exchange using iodides such as HI, KI or alkaline metal salts of iodine (K. Matsuoka, [Elements of Iodine] supplemented and revised second edition, 1992, published by Kasumigaseki Shuppan Co., Ltd.).

Described as a direct iodination method in [Elements of Iodine] described above are, for example, a method in which a substrate is dissolved in sulfuric acid and in which iodine is added thereto, a method in which a substrate is dissolved in sulfuric acid and in which alkali iodide and alkali iodate are added thereto to generate iodine in the system and a method in which sulfur iodide and nitric acid are used to iodinate an aromatic ring. In the above methods, however, the selectivity and the yield in the reactions are not necessarily satisfactory, and an iodination method which can be applied to various substrates and is effective is not described in [Elements of Iodine].

To give the examples of a case where aromatic carboxylic acids are iodinated, they include a direct iodination method of benzoic acid using iodine monochloride and silver sulfate in sulfuric acid (Synthesis, No. 5, p. 748, 1999), a direct iodination method of benzoic acid using sulfuric acid and iodine monochloride in the same manner (Russian Journal of Org. Chem., 34 (7), 1988) and methods using manganese dioxide, potassium permanganate or nitric acid as oxidizing agents together with iodine in acetic acid (a method using $MnO_2$ and $KMnO_4$: Bull. Chem. Soc. Japan, vol. 72, p. 115, 1999, a method using $HNO_3$: Zh. Obsch. Khim. Obshchest, vol. 17, p. 464, 1972 and a method using $H_2SO_4$: J. Am. Chem. Soc., vol. 90, p. 6187, 1968).

However, among the methods described above using sulfuric acid, the direct iodination method of benzoic acid using iodine monochloride and silver sulfate have such problems on practical use that a selectivity is low even if the reaction is carried out at a low temperature in the vicinity of 0° C. and a yield is merely 57% and that in addition thereto, expensive silver sulfate has to be used.

Relatively inexpensive iodine monochloride is used in the direct iodination method using sulfuric acid and iodine monochloride, but the yield of the reaction is merely about 43%. In addition thereto, chlorides in addition to iodides are produced in many cases, and it is difficult to selectively carry out the iodination reaction.

Further, in the methods using manganese dioxide, potassium permanganate or nitric acid as oxidizing agents together with iodine in acetic acid, expensive silver sulfate is not used in an acetic acid solvent, and it can relatively easily be carried out, but both of the selectivity and the yield in the reaction can not be satisfied.

It is proposed to use zeolite in order to allow halogenation, particularly the halogenation reaction of aromatic compounds without limiting to iodination reaction to selectively proceed. Proposed are, for example, a method in which zeolite is used in chlorinating benzene and monochlorobenzene with chlorine gas to produce paradichlorobenzene (Japanese Patent Laid-Open No. 213815/2001), a method in which zeolite Y and L are used for producing methyl chloride by oxychlorinating methane in a vapor phase (Japanese Patent Laid-Open No. 227850/1992) and a method for producing paradichlorobenzene in which L type zeolite is used to chlorinate benzene in the coexistence of molecular oxygen (Japanese Patent Laid-Open No. 253929/1992).

The selectivity is observed to be improved by using zeolite in the methods described above, but it is not necessarily a satisfactory level. In addition thereto, when a halogen atom is changed from chlorine to bromine, the same selectivity can scarcely be expected. It is the existing situation that selective halogenation techniques having a high general usability are not still present. Further, a method for improving selectivity in iodination reaction by using zeolite is proposed as well. Available are, for example, a method in which toluene is reacted with iodine monochloride in the presence of zeolite (Catalysis Letters, vol. 40, p. 257, 1996), a method in which naphthalene is subjected to vapor phase oxyiodination to produce iodonaphthalenes (Journal of Catalysis, vol. 147, p. 186, 1994) and a method in which p-di-iodobenezene is produced from benzene or iodobenezene (Japanese Patent Laid-Open No. 219241/1984).

However, in the method described above in which toluene is reacted with iodine monochloride in the presence of zeolite, since iodine monochloride is used for the reaction, the reaction product is a mixture of chlorides and iodides, and the selectivity is not necessarily high. The method in which naphthalene is subjected to vapor phase oxyiodination to produce iodonaphthalenes and the method in which p-di-iodobenezene is produced from benzene or iodobenezene relate to oxyiodination by a vapor phase method, and the conversion do not reach 50%.

Further, a method in which zeolite X, Y, and L are used to isomerize aromatic iodine compounds is proposed as well (Japanese Patents No. 2559483 and No. 2559484). The intended products are obtained in the above methods, but isomers other than the intended products considerably abound in kinds and amounts, and they reside in the level that the selectivity is not necessarily excellent.

Thus, it is known in conventional techniques that if zeolite is used in direct iodination in a liquid phase, oxyiodination in a vapor phase and isomerization reaction of aromatic iodides, the selectivity is relatively improved, but effective methods for introducing iodine are unexpectedly few, and it is the existing situation that particularly iodination methods having a high selectivity which can be applied to aromatic compounds having a functional group are not observed.

The first object of the present invention is to provide an iodination method which can allow desired iodination reaction to proceed highly selectively and efficiently and which is excellent in general usability and can industrially be carried out.

Next, known as a synthetic method for 5-iodo-2-methylbenzoic acid are a method in which iodine is reacted with 2-methylbenzoic acid in the coexistence of sodium nitrite and fuming sulfuric acid (Journal of the Indian Chemical Society, p. 503 to 504, 1930) and a method in which potassium iodide is reacted with 2-methylbenzoic acid in the coexistence of thallium (III) trifluoroacetate (Journal of the Chemical Society, Perkin Transactions I., p. 2405 to 2409, 1974). However, the yield is as very low as 18% in the former method, and the latter method has the problems that the yield is as low as 33% and that in addition thereto, the thallium salt having a strong toxicity is used. Both methods are unsuitable for an industrial process for 5-iodo-2-methylbenzoic acid.

Considered to be applied as a production process for 5-iodo-2-methylbenzoic acid are, in addition to the methods described above, a so-called Sandmeyer reaction which is usually known as an iodination technique of aromatic compounds and in which aromatic amines are subjected to dediazo-iodination (Organic Syntheses, Collective Volume II, p. 351, 1943), a halogen exchange method in which chlorination or bromination is once carried out and in which iodine exchange reaction is then carried out (Organic Syntheses, Collective Volume V, p. 478, 1973) and a method in which iodine monochloride is reacted (Russian Journal of Organic Chemistry, 34 (7), p. 997 to 999, 1998). Among them, the Sandmeyer and the halogen exchange method require multistage steps, and therefore the procedures are complicated, so that they have many problems as an industrial means. The process using iodine monochloride can be expected to be carried out as a simple method in which the reaction is carried out in one step, but it has a low reactivity in reaction with aromatic compounds having an electron-withdrawing group such as benzoic acids, and high performance is not expected. For example, in Russian Journal of Organic Chemistry described above, the iodination reaction of benzoic acid is carried out, and a yield of 3-iodo-benzoic acid remain about 43%, so that if it is applied to the iodination of 2-methylbenzoic acid, the high yield can not be expected.

In the production of 5-iodo-2-methylbenzoic acid, 3-iodo-2-methylbenzoic acid which is the isomer is by-produced, and it is difficult to separate 5-iodo-2-methylbenzoic acid therefrom and purify it. Accordingly, involved therein is the problem that the product purity and the isolation yield are damaged, but a method for reducing the by-production of regioisomers is not shown in any of the conventional techniques shown above. Known as a technique for regioselectively iodinating aromatic compounds are a method in which iodine monochloride is reacted in the coexistence of zeolite (Catalysis Letters, vol. 40, p. 257, 1996), a method in which oxyiodination is carried out in the coexistence of zeolite (Japanese Patent Laid-Open No. 219241/1984 and Japanese Patent Laid-Open (through PCT) No. 502819/1989), but a selectivity of the reaction in either of them dose not necessarily reside in a satisfactory level, and the reaction examples of compounds such as 2-methylbenzoic acid having an electron-withdrawing group are scarcely known.

The second object of the present invention is to provide an industrial production means by which a product having a high purity can readily be obtained by carrying out selective iodination in iodinating 2-methylbenzoic acid to produce high purity 5-iodo-2-methylbenzoic acid and which comprises a simple procedure.

DISCLOSURE OF THE INVENTION

Intensive researches repeated by the present inventors in order to solve the problems described above have resulted in finding that suitable use of specific oxygen acids such as iodic acid and periodic acid as an oxidizing agent in the coexistence of a porous material having a regular pore structure, for example, a microporous material such as β type zeolite and the like makes it possible to selectively iodinate not only aromatic hydrocarbons but also widely ranging substrates such as halides and carboxylic acids, that the reaction proceeds selectively by carrying out iodination using 2-methylbenzoic acid as a substrate in the coexistence of a microporous material, for example, β type zeolite, iodine and iodic acid and/or periodic acid and that 5-iodo-2-methylbenzoic acid having a high purity is readily obtained by combining a simple purification step such as crystallization by addition of water or cooling. Thus, they have reached the present invention.

That is, the present invention relates to a production method for an iodine compound and a production process for 5-iodo-2-methylbenzoic acid having a high purity.

(1) A production method for an iodine compound, wherein iodine is reacted with a substrate in the presence of a porous material having a pore diameter of 500 nm or less or in the presence of the above porous material and an oxidizing agent.

(2) A production method for an iodine compound as described in the above item (1), wherein the porous material is a microporous material having a pore diameter of 0.5 to 2 nm.

(3) A production method for an iodine compound as described in the above item (1), wherein the porous material is a β type zeolite or a β type zeolite which may contain elements other than Si, Al and O constituting the framework.

(4) A production method for an iodine compound as described in the above item (1), wherein the porous material is a mesoporous material having a pore diameter exceeding 2 nm.

(5) A production method for an iodine compound as described in the above item (1), wherein the oxidizing agent is at least one compound selected from oxygen acids consisting of iodic acid, periodic acid, persulfuric acid, persulfate, nitric acid and molecular oxygen.

(6) A production method for an iodine compound as described in the above item (1), wherein the substrate is composed of at least one compound selected from aromatic hydrocarbons, condensed polycyclic aromatic hydrocarbons, polycyclic aromatic hydrocarbons, hydrocarbon having a heterocycle represented by the following formula (1), or derivatives thereof:

 (1)

(wherein R represents a hydrogen atom, a halogen atom, an alkyl group which may have a substituent, a cycloalkyl group or an aryl group; Ar represents an aromatic monocycle, a polycyle or a condensed ring, or an aromatic group having a polycyclic structure or a heterocyclic group; X represents a hydrogen atom, a halogen atom or a functional group selected from a carboxyl group, a formyl group, a hydroxyl group, a nitro group, a hydroxymethyl group, a cyano group, an amino group, an alkyloxy group, an alkyloxycarbonyl group, an acyl group, an acyloxy group, an alkylsulfonyl group and an alkylsulfonyloxy group; and R and X may be the same or a plurality thereof may be present).

(7) A production method for an iodine compound as described in the above item (6), wherein the substrate is composed of at least one compound selected from benzene, fluorobenzene, chlorobenzene, bromobenzene, benzonitrile, phthalonitrile, isophthalonitrile, toluene, xylene, cumene, biphenyl, naphthalene, anthracene, methylnaphthalene, dimethylnaphthalene, methylbenzoic acid, dimethylbenzoic acid, biphenylcarboxylic acid, biphenyldicarboxylic acid, naphthalenecarboxylic acid and naphthalenedicarboxylic acid.

(8) A production method for an iodine compound as described in the above item (2), wherein iodine is reacted with 2-methylbenzoic acid in the presence of a microporous material having a pore diameter of 0.5 2 nm and iodic acid and/or periodic acid.

(9) A production process for high purity 5-iodo-2-methylbenzoic acid, characterized by comprising an iodination reaction step carried out by the method described in the above item (8), a crystal precipitation and separation step in which a product is precipitated by adding water or cooling and then separating and a purification step in which crystal separated is recrystallized using an organic solvent.

(10) A production process for high purity 5-iodo-2-methylbenzoic acid as described in the above item (9), wherein the solvent used for recrystallization is selected from any of acetic acid, an acetic acid-water mixed solvent, 2-propanol and a 2-propanol-water mixed solvent.

(11) High purity 5-iodo-2-methylbenzoic acid produced by the process as described in the above item (9), wherein the purity is 99% or more, and the total amount of iodine, iodine compounds, inorganic salts and transition metal compounds which are contained as impurities is 500 ppm or less

BEST MODE FOR CARRYING OUT THE INVENTION

First, the production method of the present invention for an iodine compound is characterized by reacting iodine with a substrate in the presence of a porous material having a pore diameter of 500 nm or less or in the presence of the above porous material and an oxidizing agent.

Aromatic hydrocarbon, condensed polycyclic aromatic hydrocarbon, polycyclic aromatic hydrocarbon, hydrocarbon having a heterocycle represented by the following formula (1) or a derivative thereof, is suitably used for the substrate used for the production method of the present invention for an iodine compound:

 (1)

In the formula (1), R represents a hydrogen atom, a halogen atom, an alkyl group which may have a substituent, a cycloalkyl group or an aryl group. The above alkyl group, cycloalkyl group or aryl group is a saturated, unsaturated, aliphatic or alicyclic alkyl having 1 to 32 carbon atoms such as methyl, ethyl, n-propyl, iso-propyl, butyl, pentyl, hexyl, heptyl, octyl, 2-ethylhexyl, decyl, cyclohexyl, bicyclohexyl, norbornyl and decalyl. They may have functional groups such as halogen, a hydroxyl group, a nitro group, an amino group and a sulfonyl group. The halogen atom is fluorine, chlorine, bromine or iodine.

In the formula (1), X represents a hydrogen atom, a halogen atom, a carboxyl group, a hydroxyl group, a nitro group, a hydroxymethyl group, a cyano group, an amino group, an alkyloxy group, an alkyloxycarbonyl group, an acyl group, an acyloxy group, an alkylsulfonyl group or an alkylsulfonyloxy group; and R and X may be the same or a plurality thereof may be present.

Ar represents an aromatic monocycle, a polycyle or a condensed ring, or an aromatic group having a polycyclic structure or a heterocyclic group.

That is, aromatics which may have substituents or hydrocarbons having a heterocycle, halogenated hydrocarbons, carboxylic acids, nitriles and alcohols correspond to the substrate represented by the formula (1). To be more specific, they include benzene, fluorobenzene, chlorobenzene, bromobenzene, benzonitrile, phthalonitrile, isophthalonitrile, toluene, xylene, cumene, biphenyl, naphthalene, anthracene, methylnaphthalene, dimethylnaphthalene, methylbenzoic acid, dimethylbenzic acid, biphenylcarboxylic acid, biphenyldicarboxylic acid, naphthalenecarboxylic acid and naphthalenedicarboxylic acid.

An unsaturated double bond may be contained in a part of the molecular structure of the substrate as is the case with cyclohexene and thiophene, and an unsaturated triple bond may be contained therein. It is a matter of course that the present invention shall not be restricted only to the above specific examples.

In the production method of the present invention for an iodine compound, the porous material having a pore diameter of 500 nm or less is used together with the substrate. This porous material is a compound having a pore diameter of a nanometer order among macroporous materials, mesoporous materials and microporous materials each having a so-called regular pore structure.

Such structural material includes zeolite which is a microporous material having so far been well known. The specific examples thereof include, by IUPAC code, ABW, AEI, AFX, APC, ATN, ATT, ATV, AWW, CHA, DDR, EAB, ERI, GIS, JBW, KFI, LEV, LTA, MER, MON, PAU, PHI, RHO, RTE, RTH and VNI each having an eight-membered ring structure, CHI, LOV, RSN and VSV each having a nine-membered ring structure, DAC, EPI, FER, LAU, MEL, MFI, MFS, MTT, NES, TON and WEI each having a ten-membered ring structure and AFS, AFY, ATO, CAN, GME, MAZ, MEI, MTW, OFF RON and VET each having a twelve-membered ring structure. To be more specific, they include Chabazite, zeolite A, X, Y and L, mordenite and β type zeolite. The compounds having a pore diameter of 0.5 to 2 nm are preferred, and β type zeolite is particularly preferred.

Preferred is β type zeolite in which a ratio of an Si atom to an Al atom each constituting a framework is 5 or more, and β type zeolite in which it is 10 to 30 is particularly preferred. β type zeolite in which a ratio of an Si atom to an Al atom exceeds 30 can be used as well without any problems. Suitably used as well are the compounds in which framework atoms are substituted with other atoms or the compounds into which atoms other than the framework atoms, for example, Na, K, Cs, Ca, Mg, Ti, Sn, Fe, Ni, Zn, Pd, Ag and the like are introduced by means such as ion exchange and impregnation.

A mesoporous material having such a large pore diameter as exceeding 2 nm is preferably used depending on the size of the substrate. Given as the examples thereof are, for example, mesoporous silica such as FSM-16, KSW-1 and KSW-2, MCM-41, MCM-48 and MCM-50 which are generally called MS41S, mesoporous alumina, mesoporous titania and mesoporous organic silica hybrid.

In the production method of the present invention for an iodine compound, the oxidizing agent is used for the purpose of elevating the reactivity of iodine. Preferred as the oxidizing agent are iodic acid, periodic acid, nitric acid, persulfuric acid, persulfuric acid salts such as sodium persulfate, potassium persulfate and ammonium persulfate, oxygen acid salts comprising hydrogen peroxide and molecular oxygen, and iodic acid or periodic acid is particularly preferred. The substrate is preferably iodinated by a system comprising β type zeolite and iodic acid or periodic acid out of the above compounds and a system comprising them and, if necessary, mineral acid such as sulfuric acid or nitric acid.

It is possible to carry out iodination reaction by a batch system, a semi-batch system or a continuous system, and it can be carried out in a system of a liquid phase or a gas phase. However, iodination other than oxyiodination is usually carried out preferably in a liquid phase in terms of efficient use of a reactor.

The amount of iodine used for iodination reaction is preferably 0.5 mole or more per mole of the substrate targeted, but it may be reacted in a stoichiometrically excessive or short state.

The amount of the microporous material and the mesoporous material such as zeolite which are porous material having a regular pore structure falls preferably in a range of 0.05 to 0.5 part by weight per 1 part by weight of the substrate. However, if 0.5 part by weight or more is used, specific troubles excluding the economical efficiency shall not be provided.

The oxidizing agent is used in a range of preferably 0.01 to 1 mole, particularly preferably 0.1 to 0.5 mole based on the substrate. Mineral acid can be used in combination with iodic acid or periodic acid which is preferred as the oxidizing agent for the purpose of improving the conversion of the substrate. If a use amount of mineral acid is increased, the selectivity of the reaction is reduced, and therefore excess use thereof is not preferred. When mineral acid such as sulfuric acid or nitric acid is used in combination with iodic acid or periodic acid, a use amount thereof is preferably 10% by weight or less, particularly preferably 1 to 2% by weight based on the substrate.

A solvent does not necessarily have to be used in order to accelerate the iodination reaction, but the solvent is preferably used for the purposes of an improvement in the reaction performance and in the stirring effect and an inhibition in a rise of the temperature. The preferred solvent is aliphatic hydrocarbons, aromatic hydrocarbons, halogenated hydrocarbons, aromatic halogenated hydrocarbons, nitrites, ethers, carboxylic acids and water, and it can suitably be selected from them and used. When iodic acid or periodic acid is used as the oxidizing agent, the particularly preferred solvent is acetic acid. Usually, the solvent is used in an amount of 2 to 10 times volume based on the substrate, but a use amount of the solvent may fall outside the above range.

In the production method of the present invention for an iodine compound, the raw materials such as the substrate, iodine and the oxidizing agent and the zeolite catalyst which is a regular porous material can be charged in one lot to carry out the reaction. The raw materials such as the substrate, iodine and the oxidizing agent may be added separately or in succession. Usually, the reaction temperature is preferably 250° C. or lower, particularly preferably 80 to 200° C. in the case of liquid phase reaction. A temperature range of 200 to 400° C. is preferred in the case of gas phase reaction. After finishing the iodination reaction, usual separating and purification steps such as filtration, solvent removal and crystallization can be carried out to obtain the intended purified product.

In the present invention, when 2-methylbenzoic acid is used as the substrate to produce high purity 5-iodo-2-methylbenzoic acid which is useful for medicines, electronic materials, functional materials and the like, it can efficiently be produced by combining the iodination reaction step with a step for depositing the product by adding water or cooling and a purification step by recrystallization using water and an organic solvent such as 2-propanol.

2-Methylbenzoic acid of the substrate which is used as the raw material for 5-iodo-2-methylbenzoic acid shall not specifically be restricted as long as it is industrially available, and the compound having a purity of 98% or more is preferably used in order to raise a purity of the final product.

The production method for an iodine compound described above is used for the iodination reaction step in producing high purity 5-iodo-2-methylbenzoic acid, and the microporous material described above, particularly β type zeolite is preferred as the porous material.

In carrying out the iodination reaction of 2-methylbenzoic acid, it is carried out in the coexistence of iodic acid and/or periodic acid in addition to iodine in the presence of the microporous material. The iodination reaction proceeds only with iodine, but a compound having an electron-withdrawing group such as 2-methylbenzoic acid has a low reactivity, and therefore the reactivity has to be raised by allowing iodic acid and/or periodic acid to coexist. Also, the reactivity can further be elevated by suitably adding mineral acid such as sulfuric acid or nitric acid.

In the above iodination reaction step, any of iodine, iodic acid and periodic acid is solid at a room temperature, and they may be used as they are solid in using them for the reaction or they may be dissolved or suspended in a suitable solvent and then used.

In carrying out the iodination reaction, various reaction systems such as a batch system, a semi-batch system, a complete mixing flow system and a fixed bed flow system can be used. The reaction system may be selected according to the production scale. In the case of the production in a small quantity, a batch system is suited, and when carrying out the production in a large quantity, it is more efficient production method to continuously carry out the reaction by a complete mixing flow system or a fixed bed flow system.

The reaction temperature in the iodination reaction of 2-methylbenzoic acid falls in a range of 50 to 200° C., preferably 70 to 150° C. Also when the temperature is lower than the above range, the reaction proceeds, but the satisfactory reaction rate is not obtained. When the temperature is higher than the above range, side reactions such as production of higher boiling components are increased, and therefore it is not preferred. The reaction pressure falls in a range of 0.05 to 20 atm, preferably 0.1 to 10 atm in terms of absolute pressure.

A melting point of 2-methylbenzoic acid is 105° C., and when the reaction is carried out at a temperature higher than the melting point, a reaction solvent is not necessarily required. Usually, an organic solvent which is inactive to iodination is preferably used, and used are acetic acid, trifluoroacetic acid, dichloromethane, carbon tetrachloride, dichlorobenzene and chlorobenzene. A use amount of the solvent falls in a range of preferably 0.5 to 100 parts by weight, more preferably 1 to 50 parts by weight per 1 part by weight of 2-methylbenzoic acid.

A use amount of iodine in the iodination reaction of 2-methylbenzoic acid shall not specifically be restricted, and it is 0.5 mole or more, preferably 1 mole or more per mole of 2-methylbenzoic acid in order to enhance the conversion of 2-methylbenzoic acid. A use amount of iodic acid and/or periodic acid falls in a range of preferably 0.01 to 1 mole, more preferably 0.05 to 0.5 mole per mole of iodine.

A use amount of the microporous material is 0.05 part by weight or more, preferably 0.1 part by weight or more per 1 part by weight of 2-methylbenzoic acid which is the substrate. If a use amount of the microporous material is smaller than the above range, the satisfactory reaction activity is not obtained, and 5-iodo-2-methylbenzoic acid can not selectively be obtained. When the microporous material is suspended to carry out the reaction, the reaction mixture obtained after the reaction can readily be separated from the microporous material by a conventional method such as settling, centrifugal separation, filtration and the like. The microporous material separated may be recycled to the reaction system, and in such case, it may be recycled after carrying out necessary treatments such as removal of adhered organic materials by washing with a suitable solvent or burning in the air.

In the iodination reaction of 2-methylbenzoic acid, addition of mineral acid such as sulfuric acid and the like to the reaction system described above makes it possible to accelerate more the reaction speed. In this case, an amount of the mineral acid added is suitably 0.005 to 0.05 part by weight per 1 part by weight of 2-methylbenzoic acid. If an addition amount of the mineral acid is smaller than the above range, the accelerating effect of the reaction speed is scarcely provided. When it is larger than the above range, side reactions are liable to be caused to damage the selectivity to intended 5-iodo-2-methylbenzoic acid, and therefore it is not preferred.

In carrying out the iodination reaction of 2-methylbenzoic acid, a reaction system such as a batch system, a semi-batch system and a complete mixing flow system is adopted, and 1 to 20 hours are usually adopted as the reaction time in the batch system and the semi-batch system and the residence time in the complete mixing flow system. In the case of the fixed bed flow system, 0.05 to 1 $h^{-1}$ is usually adopted as LHSV (liquid space velocity).

The production process for high purity 5-iodo-2-methylbenzoic acid according to the present invention comprises the iodination reaction step described above, a crystal precipitation and separation step in which the product is precipitated by adding water or cooling and then separated and a purification step in which crystal separated is recrystallized using an organic solvent. That is, 5-iodo-2-methylbenzoic acid can be isolated by adding water to the reaction mixture or cooling the reaction mixture after carrying out the reaction by the said process, and purifying operation is further carried out by recrystallization of the crystal isolated, whereby high purity 5-iodo-2-methylbenzoic acid can be obtained.

In a crystal-recovering step, 5-iodo-2-methylbenzoic acid is precipitated by adding 1 to 10 parts by weight of water per 1 part by weight of the reaction mixture, and it is recovered by filtration. When adding water, iodine is precipitated and mixed with 5-iodo-2-methylbenzoic acid in a certain case, and iodine can be prevented from being precipitated by adding sodium sulfite or sodium thiosulfate in advance to the reaction mixture. An addition amount of sodium sulfite or sodium thiosulfate is sufficiently 0.05 part or less per 1 part by weight of iodine used for the reaction. The crystal can be recovered by cooling the reaction mixture to 90° C. or lower in addition to the method of adding water. After cooling to 90° C. or lower, the crystal precipitated is recovered by filtration.

The crystal recovered is purified by recrystallizing from an organic solvent. The organic solvent used for the recrystallization may be any one as long as it dissolves 5-iodo-2-methylbenzoic acid. Suitably used are acetic acid, an acetic acid-water mixed solvent, 2-propanol and a 2-propanol-water mixed solvent. A use amount of the solvent is suitably 1 to 30 parts by weight, preferably 5 to 20 parts by weight per 1 part by weight of the crystal recovered. The recrystallization operation is carried out by heating the crystal recovered and the solvent at 40° C. or higher and mixing them to completely dissolve it and then cooling the solution to precipitate crystal. The cooling temperature is set to a temperature which is lower by 20° C. or more than the temperature at which the crystal is completely dissolved in heating and mixing. The crystal precipitated is recovered by filtration and dried, and then the product is obtained.

5-Iodo-2-methylbenzoic acid obtained by the process described above can be provided with such a very high purity that a purity is 99% or more and that the total amount of iodine, iodine compounds, inorganic salts and transition metal compounds which are contained as impurities is 500 ppm or less In the production method of the present invention for an iodine compound, iodine can be introduced into various substrates at a high selectivity, and in the case of other substrates than 2-methylbenzoic acid, the iodine compounds having less impurities can be obtained as well by almost the same operation.

Next, the present invention shall more specifically be explained with reference to examples. However, the present invention shall by no means be restricted by the following examples.

A. Iodination of Aromatic Carboxylic Acid

EXAMPLE 1

2-methylbenzoic Acid

A three-necked flask of 200 mL equipped with a reflux condenser and a stirrer was charged with acetic acid (100 g), H-β zeolite (4.6 g), iodine (20.2 g, 0.16 mol), 2-methylbenzoic acid (20 g, 0.15 mol), periodic acid dihydrate (7.3 g, 0.03 mol) and sulfuric acid (0.24 g), and they were sufficiently mixed and stirred at a room temperature. The mixture temperature was raised up to 110° C. on a mantle heater, and then the reaction was carried out for one hour. Further, the reaction was carried out at refluxing temperature (about 118° C.) of acetic acid for 5 hours.

After finishing the reaction, the reaction mixture was filtered to recover H-β zeolite, and a 10 weight % sodium sulfite aqueous solution (100 mL) was added to the filtrate to treat remaining iodine. Next, water (800 g) was added thereto to precipitate crystal, and then it was filtered and recovered.

The crystal thus obtained and the filtrate were analyzed by means of HPLC (high performance liquid chromatography)

to investigate the performance enhancement, and it resulted in finding that a conversion of 2-methylbenzoic acid was 88% and the yields of the products were 72% for 5-iodo-2-methylbenzoic acid and 6% for 3-iodo-2-methylbenzoic acid. The ratio of (5-iodo/3-iodo) regioisomer was 12.

COMPARATIVE EXAMPLE 1

2-methylbenzoic Acid: a Case where H-β Zeolite was not Used

The same procedure as in Example 1 was carried out, except that H-β zeolite was not used in Example 1. A conversion of 2-methylbenzoic acid was 98%; the yields were 66% for 5-iodo-2-methylbenzoic acid and 25% for 3-iodo-2-methylbenzoic acid. The ratio of (5-iodo/3-iodo) regioisomer was 2.6.

EXAMPLE 2

3-methylbenzoic Acid

The same procedure as in Example 1 was carried out, except that 3-methylbenzoic acid (20 g, 0.15 mol) was used as the reactant in Example 1. A conversion of 3-methylbenzoic acid was 50%; the yields were 1) 40% for 6-iodo-3-methylbenzoic acid and 2) 8% for the regioisomers of other iodides; and a ratio of 1)/2) was 5.

COMPARATIVE EXAMPLE 2

3-methylbenzoic Acid: a Case where H-β Zeolite was not Used

The same procedure as in Example 2 was carried out, except that H-β zeolite was not used in Example 2. A conversion of 3-methylbenzoic acid was 56%; the yields were 1) 33% for 6-iodo-3-methylbenzoic acid and 2) 16% for the regioisomers of other iodides; and a ratio of 1)/2) was 2.1.

EXAMPLE 3

2,4-dimethylbenzoic Acid

The same procedure as in Example 1 was carried out, except that 2,4-dimethylbenzoic acid (22.5 g, 0.15 mol) was used as the reactant in Example 1. A conversion of 2,4-dimethylbenzoic acid was 98%; the yields were 1) 88% for 5-iodo-2,4-dimethylbenzoic acid and 2) 7% for the regioisomers of other iodides; and a ratio of 1)/2) was 12.6.

COMPARATIVE EXAMPLE 3

2,4-dimethylbenzoic Acid: a Case where H-β Zeolite was not Used

The same procedure as in Example 3 was carried out, except that H-β zeolite was not used in Example 3. A conversion of 2,4-dimethylbenzoic acid was 96%; the yields were 1) 81% for 5-iodo-2,4-dimethylbenzoic acid and 2) 8% for the regioisomers of other iodides; and a ratio of 1)/2) was 10.

B. Iodination of Aromatic Hydrocarbons

EXAMPLE 4

Toluene

The same procedure as in Example 1 was carried out, except that toluene (13.8 g, 0.15 mol) was used as the reactant in Example 1. A conversion of toluene was 98%; the yields were 1) 82% for 4-iodotoluene and 2) 9% for the regioisomers of other iodides; and a ratio of 1)/2) was 9.1.

COMPARATIVE EXAMPLE 4

Toluene: a Case where H-β Zeolite was not Used

The same procedure as in Example 4 was carried out, except that H-β zeolite was not used in Example 4. A conversion of toluene was 100%; the yields were 1) 56% for 4-iodotoluene and 2) 39% for the regioisomers of other iodides; and a ratio of 1)/2) was 1.4.

EXAMPLE 5 o-xylene

The same procedure as in Example 1 was carried out, except that o-xylene (15.9 g, 0.15 mol) was used as the reactant in Example 1. A conversion of o-xylene was 99%; the yields were 1) 92% for 4-iodo-1,2-dimethylbenzene and 2) 6% for the regioisomers of other iodides; and a ratio of 1)/2) was 15.

COMPARATIVE EXAMPLE 5 o-xylene: a Case where H-β Zeolite was not Used

The same procedure as in Example 5 was carried out, except that H-β zeolite was not used in Example 5. A conversion of o-xylene was 100%; the yields were 1) 78% for 4-iodo-1,2-dimethylbenzene and 2) 16% for the regioisomers of other iodides; and a ratio of 1)/2) was 4.9.

EXAMPLE 6

Biphenyl

The same procedure as in Example 1 was carried out, except that biphenyl (23.1 g, 0.15 mol) was used as the reactant in Example 1. A conversion of biphenyl was 99%; the yields were 1) 92% for 4-iodobiphenyl and 2) 5% for the regioisomers of other iodides; and a ratio of 1)/2) was 18.4.

C. Iodination of Aromatic Halogenated Hydrocarbon

EXAMPLE 7

Fluorobenzene

The same procedure as in Example 1 was carried out, except that fluorobenzene (14.4 g, 0.15 mol) was used as the reactant in Example 1. A conversion of fluorobenzene was 65%; the yields were 1) 52% for 4-iodofluorobenzene and 2) 3% for the regioisomers of other iodides; and a ratio of 1)/2) was 17.3.

COMPARATIVE EXAMPLE 6

Fluorobenzene: a Case where H-Zeolite was not Used

The same procedure as in Example 7 was carried out, except that H-β zeolite was not used in Example 7. A conversion of fluorobenzene was 63%; the yields were 1) 42% for 4-iodofluorobenzene and 2) 6% for the regioisomers of other iodides; and a ratio of 1)/2) was 7.

D. Iodination of Nitrile

EXAMPLE 8

2-methylcyanobenzene

The same procedure as in Example 1 was carried out, except that 2-methylcyanobenzene (15.5 g, 0.15 mol) was used as the reactant in Example 1. A conversion of 2-methylcyanobenzene was 82%; the yields were 1) 69% for 5-iodo-2-methylcyanobenzene and 2) 6% for 3-iodo-2-methylcyanobenzene; and a ratio of 1)/2) was 11.5.

COMPARATIVE EXAMPLE 7

2-methylcyanobenzene: a Case where H-β Zeolite was not Used

The same procedure as in Example 8 was carried out, except that H-β zeolite was not used in Example 8. A conversion of 2-methylcyanobenzene was 92%; the yields were 1) 61% for 5-iodo-2-methylcyanobenzene and 2) 24% for 3-iodo-2-methylcyanobenzene; and a ratio of 1)/2) was 2.5.

E. Iodination in a Case where an Oxidizing Agent Other than Periodic Acid was Used

EXAMPLE 9

Oxidation by Iodic Acid

The same procedure as in Example 1 was carried out, except that iodic acid (5.3 g, 0.03 mol) was substituted for periodic acid as the oxidizing agent in Example 1. A conversion of 2-methylbenzoic acid was 78%; the yields were 1) 69% for 5-iodo-2-methylbenzoic acid and 2) 3% for the regioisomers of other iodides; and a ratio of 1)/2) was 23.

COMPARATIVE EXAMPLE 8

Oxidation by Iodic Acid: a Case where H-β Zeolite was not Used

The same procedure as in Example 9 was carried out, except that H-β zeolite was not used in Example 9. A conversion of 2-methylbenzoic acid was 79%; the yields were 1) 53% for 5-iodo-2-methylbenzoic acid and 2) 23% for the regioisomers of other iodides; and a ratio of 1)/2) was 2.3.

EXAMPLE 10

Oxidation by Sodium Persulfate

The same apparatus as in Example 1 was used and charged with acetic acid (90 g), water (10 g), H-β zeolite (2.3 g), iodine (10.3 g, 0.08 mol), 2-methylbenzoic acid (10 g, 0.074 mol), sodium persulfate (11.8 g, 0.05 mol) and sulfuric acid (0.12 g). After they were sufficiently mixed and stirred at a room temperature, the mixture temperature was elevated up to 90° C., and then the reaction was carried out for 5 hours. Further, the reaction was carried out at 110° C. for 8 hours, and then the reaction was finished. H-β zeolite was separated by filtration, and remaining iodine was treated by a 10 weight % sodium sulfite aqueous solution. Then, 800 mL of water was added thereto, and crystal precipitated was filtered off.

A conversion of 2-methylbenzoic acid was 86%; the yields were 1) 64% for 5-iodo-2-methylbenzoic acid and 2) 12% for 3-iodo-2-methylbenzoic acid; and a ratio of 1)/2) was 5.3.

F. Iodination in a Case where Zeolite Other than H-β Zeolite was Used

EXAMPLES 11 TO 14

The same procedure as in Example 1 was carried out, except that mordenite, Y, L and ZSM-5 which are microporous materials each were substituted for H-β zeolite in Example 1. When using respective zeolites, The ratio of (5-iodo/3-iodo) regioisomer is shown below.

| mordenite | (Example 11) | 5.0 |
| zeolite Y | (Example 12) | 4.8 |
| zeolite L | (Example 13) | 5.2 |
| ZSM-5 | (Example 14) | 4.0 |

A ratio of (5-iodo/3-iodo) regioisomer in the case of H-β zeolite (Example 1) was 12, and that in the case where zeolite was not used (Comparative Example 1) was 2.6. It was found that the selectivity was high as well in the cases where zeolites other than H-β zeolite were used.

G. Production of High Purity 5-iodo-2-methylbenzoic Acid

EXAMPLE 15

The same procedure as in Example 1 was carried out, except that in Example 1, sulfuric acid was not used; 8.8 g of iodic acid was substituted for periodic acid; and the reaction was carried out at a refluxing temperature (115° C.) of acetic acid for 3 hours.

The results are shown below:

| conversion of 2-methylbenzoic acid | 70% |
| yield of 5-iodo-2-methylbenzoic acid | 65% |
| yield of 3-iodo-2-methylbenzoic acid | 2% |
| ratio of (5-iodo/3-iodo) regioisomer = | 33 |
| purity of 5-iodo-2-methylbenzoic acid in crystal | 97% |

5-Iodo-2-methylbenzoic acid obtained by recrystallizing the crystal of 5-iodo-2-methylbenzoic acid described above having a purity of 97% with a solvent of water:2-propanol=1:1 (weight ratio) had a purity of 99% or more.

The recrystallized product of 5-iodo-2-methylbenzoic acid described above contained 4 ppm of free iodine. This crystal was subjected to ICP all element analysis to result in finding that Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb and S were not detected and that all the elements of group 1 and group 2 in the periodic table had a content of 1 ppm or less.

EXAMPLE 16

A 100 mL three-necked flask equipped with a reflux condenser was charged with acetic acid 50 g, 2-methylbenzoic acid 10 g, iodine 10.4 g, periodic acid 3.7 g, H-β zeolite 2.2 g and sulfuric acid 0.12 g, and they were reacted at a refluxing temperature (115° C.) of acetic acid for 6 hours. After finishing the reaction, H-β zeolite was separated by filtration, and 20 g of a 10 weight % sodium sulfite aqueous solution and 250 mL of water were added to the filtrate and cooled down to a room temperature. Crystal precipitated was recovered by filtration to obtain 15 g (weight after drying) of a product. The crystal recovered and the mother liquor was analyzed by means of HPLC (high pressure liquid chromatography) to evaluate in obtaining the following results:

| | |
|---|---|
| conversion of 2-methylbenzoic acid | 85% |
| yield of 5-iodo-2-methylbenzoic acid | 70% |
| yield of 3-iodo-2-methylbenzoic acid | 7% |
| ratio of (5-iodo/3-iodo) regioisomer = | 10 |
| purity of 5-iodo-2-methylbenzoic acid in crystal | 95% |

EXAMPLE 17

A recovered product 13 g was obtained by the same method as in Example 16, except that 4.3 g of iodic acid was substituted for periodic acid. As a result of analysis, the following data were obtained:

| | |
|---|---|
| conversion of 2-methylbenzoic acid | 80% |
| yield of 5-iodo-2-methylbenzoic acid | 72% |
| yield of 3-iodo-2-methylbenzoic acid | 3% |
| ratio of (5-iodo/3-iodo) regioisomer = | 24 |
| purity of 5-iodo-2-methylbenzoic acid in crystal | 95% |

EXAMPLE 18

Cooling Crystallization

Reaction was carried out on the same conditions as in Example 16, except that an amount of acetic acid was changed to 40 g, and the filtrate was cooled down to a room temperature after H-β zeolite was separated. Crystal precipitated was recovered by filtration to obtain 10 g of a product. As a result of analysis, the following data were obtained:

| | |
|---|---|
| conversion of 2-methylbenzoic acid | 88% |
| yield of 5-iodo-2-methylbenzoic acid | 72% |
| yield of 3-iodo-2-methylbenzoic acid | 8% |
| ratio of (5-iodo/3-iodo) regioisomer = | 9 |
| purity of 5-iodo-2-methylbenzoic acid in crystal | 95% |

COMPARATIVE EXAMPLE 9

Iodine Monochloride (ICl) Method

Suspended in a 100 mL three-necked flask equipped with a reflux condenser were 25 mL of 30 weight % sulfuric acid and 1.36 g (10 mmol) of 2-methylbenzoic acid, and 2.4 g (15 mmol) of iodine monochloride dissolved in 5 g of acetic acid was dropwise added thereto in 40 minutes. Reaction was carried out at 90° C. for 5 hours, and the reaction mixture was poured into 90 mL of water. The precipitate was filtered and washed with a sodium sulfite aqueous solution to obtain a crystalline solid (yield: 1.6 g) as the product. This solid was analyzed to find that the product showed the following distribution:

| | |
|---|---|
| 2-methylbenzoic acid | 33% |
| 5-chloro-2-methylbenzoic acid | 13% |
| 3-chloro-2-methylbenzoic acid | 9% |
| 5-iodo-2-methylbenzoic acid | 38% |
| 3-iodo-2-methylbenzoic acid | 5% |
| others | 2% |

The above mixture was purified by recrystallization using acetic acid or isopropyl alcohol to try to isolate 5-iodo-2-methylbenzoic acid. However, a purity of the mixture was scarcely improved, and it was difficult to obtain 5-iodo-2-methylbenzoic acid.

COMPARATIVE EXAMPLE 10

NaI—NaIO$_4$/Sulfuric Acid Method

The same apparatus as in Example 16 was used to dissolve 1.36 g of 2-methylbenzoic acid in 9 mL of acetic acid. The temperature of the mixture was maintained at 85° C., and 11 ml of conc. sulfuric acid was dropwise added thereto in 25 minutes. Further, 0.6 g of sodium periodate was added thereto, and then a solution prepared by dissolving 1.1 g of sodium iodide in 5 mL of acetic acid was dropwise added thereto in 10 minutes. Thereafter, the reaction was carried out for 2 hours, and after cooling, the reaction mixture was poured into 90 mL of water and the produced muddy mixture was filtered. Sodium sulfite 1 g was added thereto to remove unreacted iodine. After drying, the product thus obtained was analyzed to result in obtaining the following data:

| | |
|---|---|
| 2-methylbenzoic acid | 35% |
| 5-iodo-2-methylbenzoic acid | 37% |
| 3-iodo-2-methylbenzoic acid | 18% |
| others | 5% |

It was tried to obtain 5-iodo-2-methylbenzoic acid from the above mixture as was the case with Comparative Example 11, but the purity was scarcely improved, and it was difficult to obtain 5-iodo-2-methylbenzoic acid.

COMPARATIVE EXAMPLE 11

No Zeolite

Reaction was carried out by the same method as in Example 16 to obtain 15 g of a product, except that H-β zeolite was not used. As a result of analysis, the following data were obtained:

| | |
|---|---|
| conversion of 2-methylbenzoic acid | 85% |
| yield of 5-iodo-2-methylbenzoic acid | 56% |
| yield of 3-iodo-2-methylbenzoic acid | 20% |
| ratio of (5-iodo/3-iodo) regioisomer = | 2.8 |
| purity of 5-iodo-2-methylbenzoic acid in crystal | 80% |

COMPARATIVE EXAMPLE 12

No Oxidizing Agent

Reaction was carried out by the same method as in Example 16 to obtain 0.8 g of a product, except that periodic acid was not used. As a result of analysis, the following data were obtained:

| | |
|---|---|
| conversion of 2-methylbenzoic acid | 5% |
| yield of 5-iodo-2-methylbenzoic acid | 3% |
| yield of 3-iodo-2-methylbenzoic acid | 0.9% |
| ratio of (5-iodo/3-iodo) regioisomer = | 3.3 |
| purity of 5-iodo-2-methylbenzoic acid in crystal | 75% |

EXAMPLE 19

Crystal Purification/Water-IPA

The crystal 15 g of 5-iodo-2-methylbenzoic acid having a purity of 95% obtained in Example 16 was dissolved in a solvent 210 g of water:2-propanol=1:1 (weight ratio) at 70° C., and the solution was kept at a room temperature for a night. Crystal 10 g precipitated was recovered by filtering and analyzed by HPLC to result in finding that 5-iodo-2-methylbenzoic acid had a purity of 99%.

The crystal 1 g obtained above having a purity of 99% was dissolved in 25 mL of methanol, and 25 mL of a 4% KI aqueous solution and 5 mL of 17% sulfuric acid were added thereto. Then, the solution was titrated with a 0.02M sodium thiosulfate aqueous solution to result in finding that 5 ppm of free iodine was contained therein. According to ICP all element analysis, Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb and S were not detected, and all the elements of group 1 and group 2 in the periodic table had a content of 1 ppm or less.

EXAMPLE 20

Crystal Purification/Acetic Acid

The crystal 10 g of 5-iodo-2-methylbenzoic acid having a purity of 95% obtained in Example 18 was dissolved in 210 g of acetic acid at 70° C., and the solution was kept at a room temperature for a night. Crystal 6 g precipitated was recovered by filtering and analyzed by HPLC to result in finding that 5-iodo-2-methylbenzoic acid had a purity of 99%.

The crystal 1 g obtained above having a purity of 99% was analyzed by the same method as in Example 19 to result in finding that 10 ppm of free iodine was contained therein. According to ICP all element analysis, Li, Na, K, Mg, Ca, Sr, Ba, Sc, Y, Ti, Zr, V, Nb, Cr, Mo, W, Mn, Fe, Ru, Co, Rh, Ni, Pd, Pt, Cu, Ag, Au, Zn, Cd, Al, In, Si, Sn, Pb, P, Sb and S were not detected, and all the elements of group 1 and group 2 in the periodic table had a content of 1 ppm or less.

INDUSTRIAL APPLICABILITY

According to the production method of the present invention for an iodine compound, iodine can be introduced into various substrates at a high selectivity. Since expensive metals and specific reagents do not have to be used, it can readily be carried out in an industrially scale, and the product having a high purity can be obtained.

Further, the process of the present invention comprising iodination reaction, separation and purification steps makes it possible to readily obtain at a high yield, 5-iodo-2-methylbenzoic acid having a high purity which is useful in uses for functional chemical products such as medicines. The steps comprising iodination reaction, separation and purification are characterized by that they are simple in terms of a procedure and that the purification load is smaller, and it is very advantageous in industrially carrying out.

What is claimed is:

1. A production method for an iodine compound, wherein iodine is reacted with a substrate in the presence of (1) a porous material having a pore diameter of 0.5 to 2 nm and (2) an oxidizing agent, in a liquid phase reaction, wherein the porous material is a H-β type zeolite, in the acid form, and the substrate is selected from the group consisting of aromatic hydrocarbons and polycyclic aromatic hydrocarbons represented by the following formula (I) or derivatives thereof:

$$R—Ar—X \quad (1)$$

(wherein R represents a hydrogen atom, a halogen atom, or an alkyl group; Ar represents an aromatic monocycle or a polycycle ring; X represents a hydrogen atom, a halogen atom or a functional group selected from the group consisting of a carboxyl group and a cyano group; and R and X may be the same or a plurality thereof may be present).

2. A production method for an iodine compound as described in claim 1, wherein the oxidizing agent is at least one compound selected from a group consisting of iodic acid, periodic acid, persulfuric acid, persulfate, and nitric acid.

3. A production method for an iodine compound as described in claim 1, wherein the substrate is selected from the group consisting of fluorobenzene, toluene, xylene, biphenyl, methylbenzoic acid and 2-methylcyanobenzene.

4. A production method for an iodine compound as described in claim 1, wherein iodine is reacted with 2-methylbenzoic acid in the presence of a microporous material having a pore diameter of 0.5 to 2 nm and iodic acid and/or periodic acid.

5. A production process for high purity 5-iodo-2-methylbenzoic acid, characterized by comprising an iodination reaction step carried out by the method described in claim 4, a crystal precipitation and separation step in which a product is precipitated by adding water or cooling and then separating and a purification step in which crystal separated is recrystallized using an organic solvent.

6. A production process for high purity 5-iodo-2-methylbenzoic acid as described in claim 5, wherein the solvent used for recrystallization is selected from any of acetic acid, an acetic acid-water mixed solvent, 2-propanol and a 2-propanol-water mixed solvent.

7. A production process for high purity 5-iodo-2-methylbenzoic acid as described in claim 5, wherein the iodination reaction step is carried out in the presence of a mineral acid.

8. A production process for high purity 5-iodo-2-methylbenzoic acid as described in claim 7, wherein said mineral acid is selected from the group consisting of sulfuric acid and nitric acid.

9. A production process for high purity 5-iodo-2-methylbenzoic acid as described in claim 7, wherein an amount of said mineral acid is 0.005 to 0.05 part by weight per 1 part by weight 2-methylbenzoic acid.

10. A production method for an iodine compound as described in claim 4, wherein the iodine is reacted with the 2-methylbenzoic acid so as to form 5-iodo-2-methylbenzoic acid.

* * * * *